United States Patent
Miller et al.

(10) Patent No.: US 8,814,914 B2
(45) Date of Patent: Aug. 26, 2014

(54) FUSION METHOD AND PEDICLE ACCESS TOOL

(75) Inventors: Peter Thomas Miller, Austin, TX (US); Charles R. Forton, Leander, TX (US); Reginald James Davis, Cockeysville, MD (US)

(73) Assignee: Zimmer Spine, Inc., Minneapolis, MN (US)

( * ) Notice: Subject to any disclaimer, the term of this patent is extended or adjusted under 35 U.S.C. 154(b) by 700 days.

(21) Appl. No.: 12/550,235

(22) Filed: Aug. 28, 2009

(65) Prior Publication Data

US 2011/0054537 A1   Mar. 3, 2011

(51) Int. Cl.
| | |
|---|---|
| A61B 17/80 | (2006.01) |
| A61B 17/70 | (2006.01) |
| A61B 17/88 | (2006.01) |
| A61F 2/46 | (2006.01) |
| A61B 17/90 | (2006.01) |
| A61B 1/32 | (2006.01) |
| A61B 17/02 | (2006.01) |

(52) U.S. Cl.
CPC .............. *A61B 17/88* (2013.01); *A61F 2/4611* (2013.01); *A61B 2017/90* (2013.01); *A61B 1/32* (2013.01); *A61B 17/8897* (2013.01); *A61B 17/0218* (2013.01)
USPC ......................................... 606/279; 606/86 A

(58) Field of Classification Search
CPC .... A61F 2/4611; A61B 2017/90; A61B 1/32; A61B 17/8893; A61B 17/0218
USPC .................. 606/246–279; 600/204, 208, 235
See application file for complete search history.

(56) References Cited

U.S. PATENT DOCUMENTS

| | | | | |
|---|---|---|---|---|
| 5,196,015 | A | * | 3/1993 | Neubardt ...................... 600/554 |
| 5,946,988 | A | | 9/1999 | Metz-Stavenhagen |
| 6,019,776 | A | * | 2/2000 | Preissman et al. ............ 606/185 |
| 6,770,079 | B2 | | 8/2004 | Bhatnagar et al. |
| 7,241,297 | B2 | | 7/2007 | Shaolian et al. |
| 7,318,826 | B2 | | 1/2008 | Teitelbaum et al. |
| 2003/0018337 | A1 | | 1/2003 | Davis |
| 2003/0050644 | A1 | | 3/2003 | Boucher et al. |
| 2004/0092988 | A1 | | 5/2004 | Shaolian et al. |
| 2005/0107800 | A1 | | 5/2005 | Frankel |
| 2006/0030872 | A1 | | 2/2006 | Culbert et al. |
| 2007/0016219 | A1 | * | 1/2007 | Levine ........................... 606/99 |
| 2007/0270896 | A1 | | 11/2007 | Perez-Cruet |
| 2008/0051793 | A1 | | 2/2008 | Erickson et al. |
| 2008/0108991 | A1 | | 5/2008 | von Jako |

(Continued)

FOREIGN PATENT DOCUMENTS

| | | |
|---|---|---|
| DE | 25 42 056 A1 | 3/1977 |
| EP | 0948939 A2 | 10/1999 |

(Continued)

*Primary Examiner* — Ellen C Hammond
*Assistant Examiner* — Stuart S Bray
(74) *Attorney, Agent, or Firm* — Seager, Tufte & Wickhem, LLC

(57) ABSTRACT

Embodiments described herein provide tools and methods for spinal fusion procedures. One embodiment of a tool can be a pedicle access tool that performs the functions of targeting needle, cannula, tap and awl. The cannula of the tool can be used to guide various tools and bone graft or fusion promoting material to a surgical site for a spinal fusion procedure, such as a posterolateral procedure. In other embodiments, a k-wire can be used as the guide.

15 Claims, 18 Drawing Sheets

(56) References Cited

U.S. PATENT DOCUMENTS

| | | |
|---|---|---|
| 2008/0114403 A1 | 5/2008 | Kuester et al. |
| 2008/0287981 A1 | 11/2008 | Culbert et al. |
| 2008/0300605 A1 | 12/2008 | Rinner |
| 2009/0138043 A1* | 5/2009 | Kohm .......................... 606/246 |
| 2009/0138044 A1 | 5/2009 | Bergeron et al. |
| 2010/0030065 A1* | 2/2010 | Farr et al. ...................... 600/424 |
| 2010/0331891 A1* | 12/2010 | Culbert et al. ................ 606/279 |
| 2011/0054537 A1* | 3/2011 | Miller et al. .................. 606/279 |
| 2011/0098628 A1* | 4/2011 | Yeung et al. ...................... 604/8 |
| 2011/0144688 A1* | 6/2011 | Reiss et al. .................... 606/192 |
| 2011/0237861 A1* | 9/2011 | Pool et al. .......................... 600/9 |
| 2012/0071929 A1* | 3/2012 | Chervitz et al. .............. 606/279 |
| 2012/0130380 A1* | 5/2012 | Babaev ............................ 606/82 |
| 2012/0221006 A1* | 8/2012 | O'Neil et al. ................... 606/79 |
| 2013/0197563 A1* | 8/2013 | Saab et al. ..................... 606/191 |
| 2013/0297025 A1* | 11/2013 | Wardlaw, Douglas ..... 623/17.12 |

FOREIGN PATENT DOCUMENTS

| | | |
|---|---|---|
| WO | 2005039423 A1 | 5/2005 |
| WO | WO2008008522 A2 | 1/2008 |
| WO | 2009073430 A2 | 6/2009 |

* cited by examiner

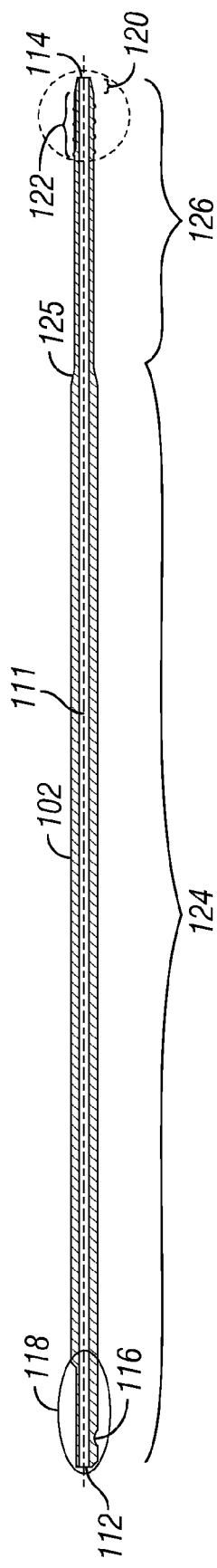
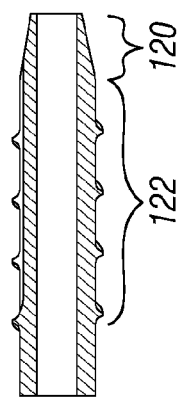
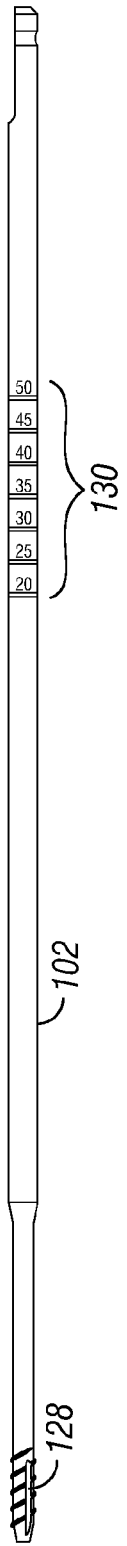
FIG. 2
FIG. 3
FIG. 4

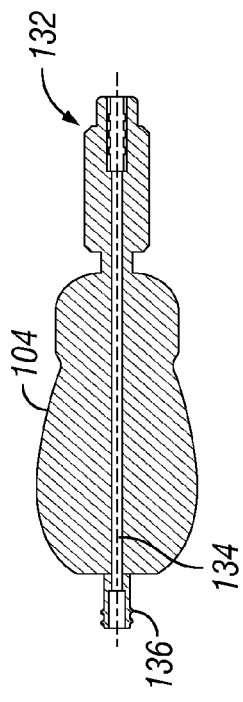
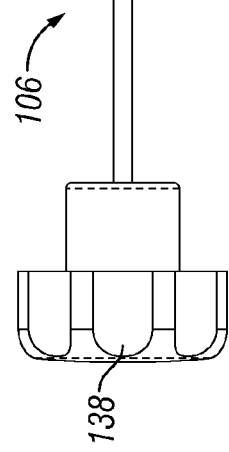
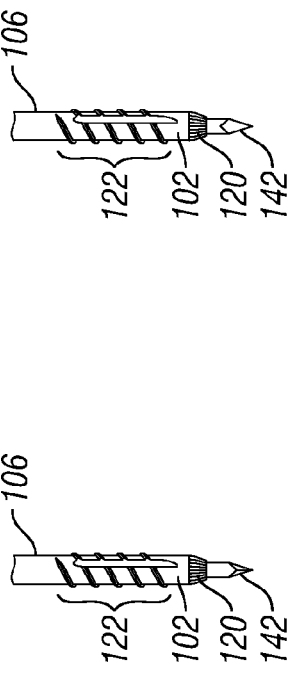
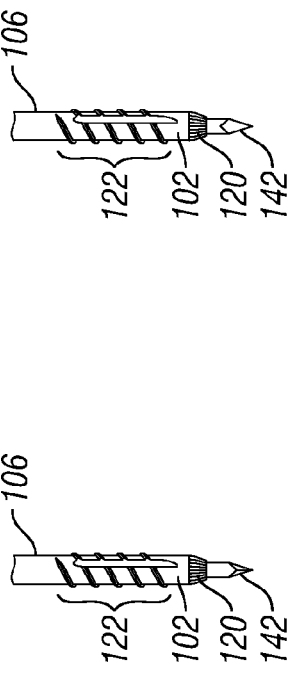
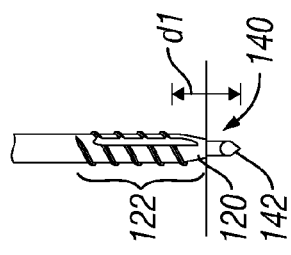

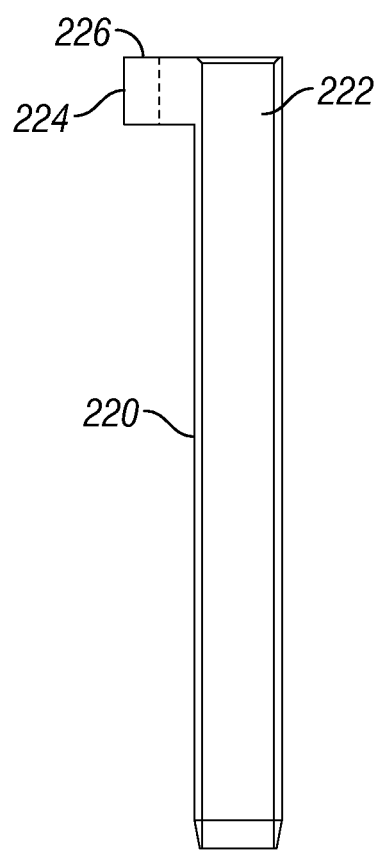 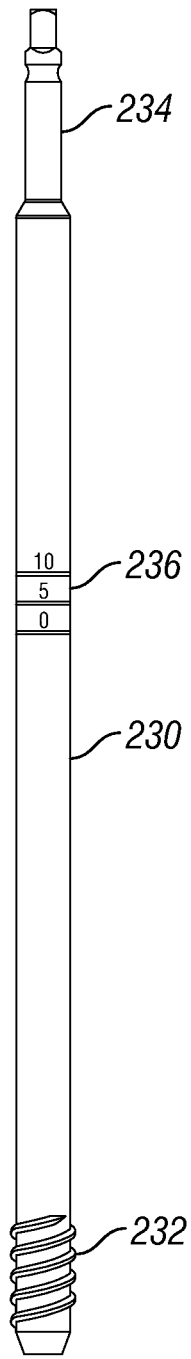
FIG. 13
FIG. 14

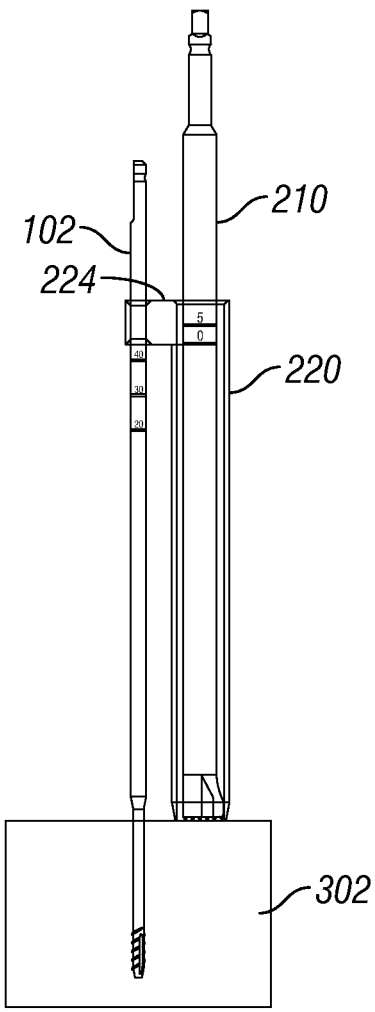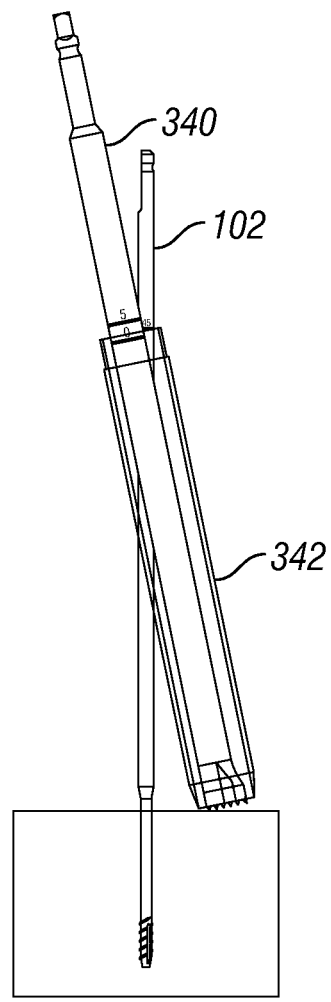
FIG. 22　　　　　　　　FIG. 23

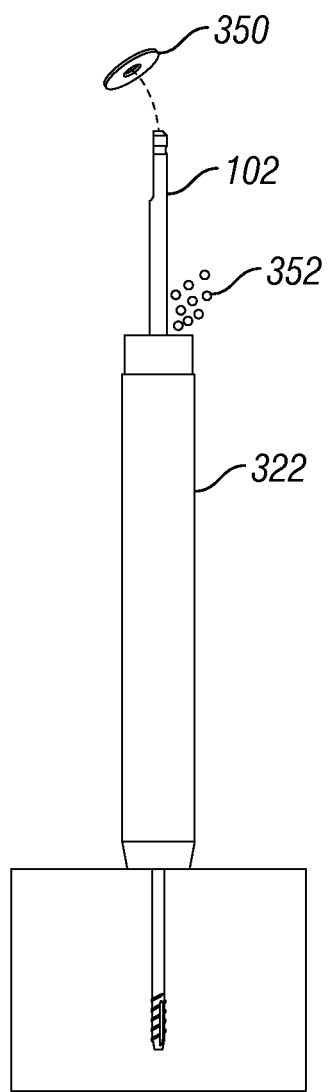
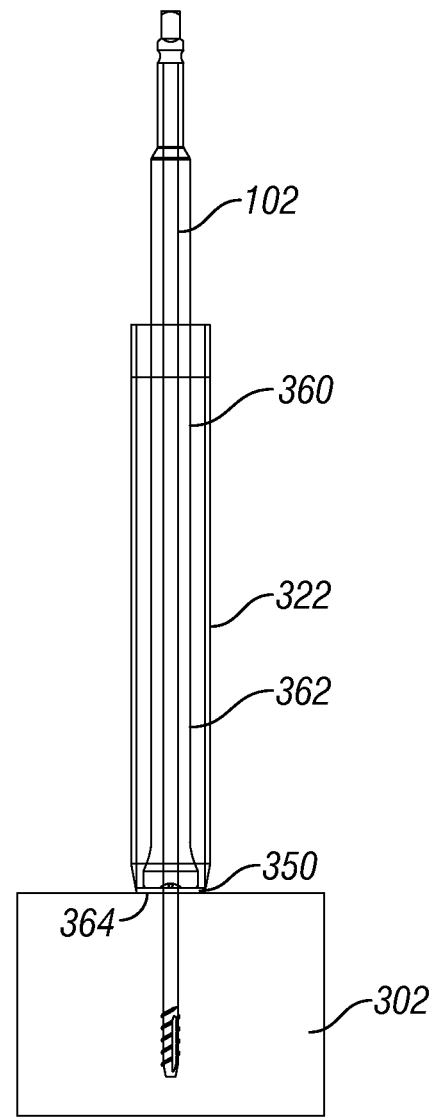
FIG. 24  FIG. 25

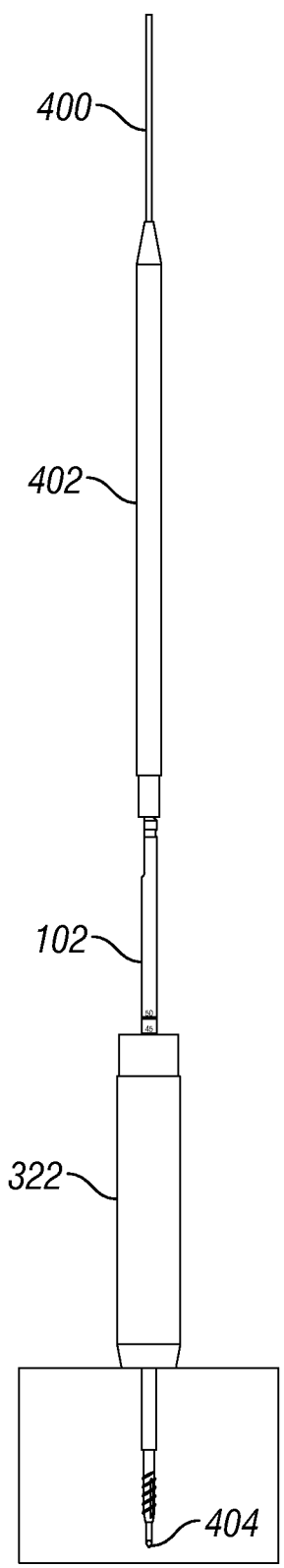
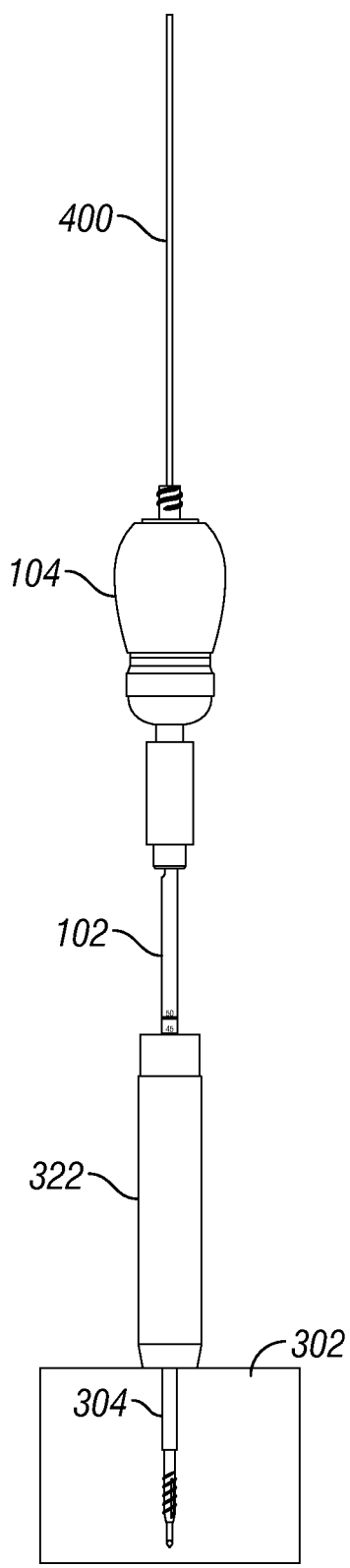
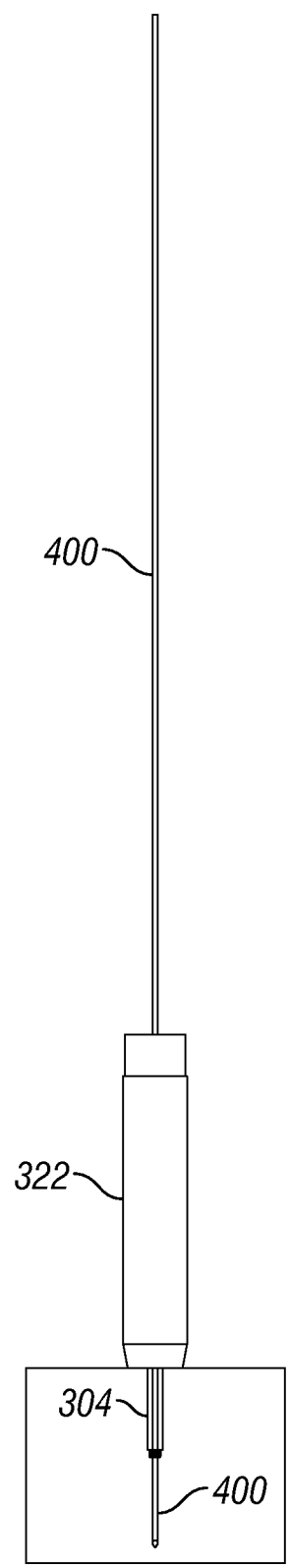
FIG. 26  FIG. 27  FIG. 28

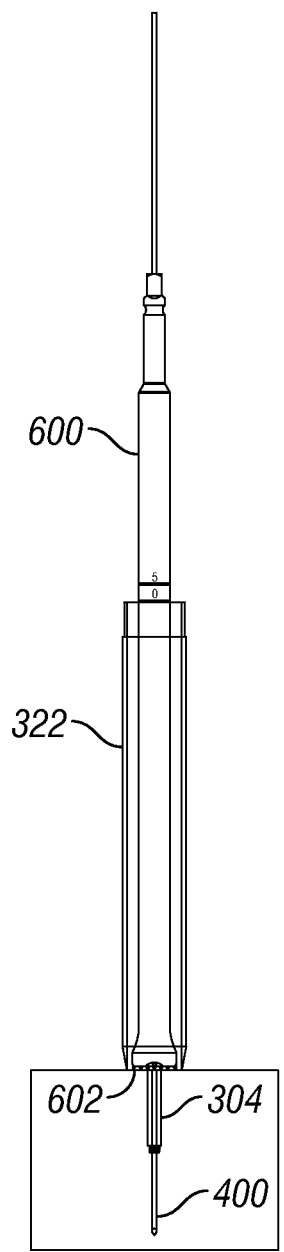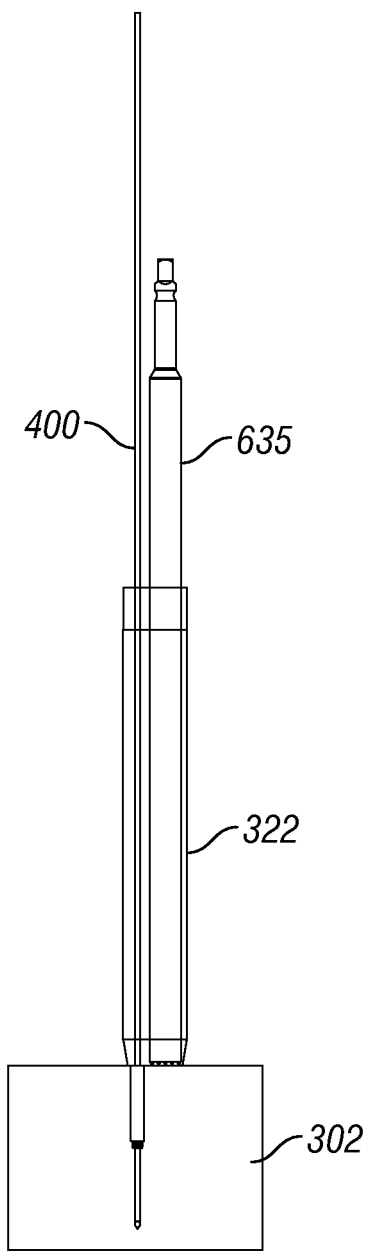
FIG. 29
FIG. 30

FUSION METHOD AND PEDICLE ACCESS TOOL

TECHNICAL FIELD

The present disclosure relates to spinal surgery tools and methods. In particular, embodiments described herein relate to a pedicle access tool and methods for performing spinal fusion procedures. Even more particularly, embodiments relate to posterolateral spinal fusion methods.

BACKGROUND

In posterolateral fusion procedures, bone graft is placed on the posterior side of the spine between the transverse processes of vertebrae. The graft promotes bone growth between the vertebrae. When the new bone is fully formed it fuses two or more vertebrae together, increasing the stability of the spine. However, it can be difficult to prepare the vertebrae so that the bone graft properly promotes fusion.

Spinal rods are used to stabilize the spine while the bone graft heals. The procedure for implanting a spinal rod often involves inserting pedicle screws that will secure the spinal rod to two or more vertebrae. To install a pedicle screw, a targeting needle that includes a stylet and cannula is advanced to a desired pedicle and tapped into the bone using a mallet. When the targeting needle is at a desired depth, the stylet is removed leaving the cannula. A k-wire is guided down the cannula and inserted into the bone. Once the guide wire is in place, the cannula is removed. A series of dilators are used to distract tissue about the k-wire. A bone awl is passed over the k-wire and used to puncture through the cortical layer of the vertebra to create a hole not exceeding the depth of the k-wire. A tap is then guided over the k-wire to tap the hole formed by the bone awl. Once the tap is removed, the bone screw can then be lead down the k-wire to the hole and screwed into place.

The tip of a k-wire is very sharp and can easily pass through bone. If the awl, tap or bone screw hit a kink in the k-wire, they can cause the k-wire to push through the vertebra further than intended. Consequently, surgeons must work slowly when guiding tools to a surgical site.

SUMMARY

Embodiments described herein provide tools and methods for spinal fusion procedures. One embodiment of a tool can be a pedicle access tool that performs the functions of targeting needle, cannula, tap and awl. One embodiment of the pedicle access tool can comprise a cannula detachably coupled to a cannula handle. The cannula can comprise a cannula body defining a passage through the cannula, a tip at the end of the cannula adapted to act as a bone awl and a threaded section disposed about the outside of the cannula to act as a bone tap. In one embodiment the cannula can have a wider section and a narrower section. A shoulder between the narrower section and wider section can act to prevent the cannula from being inserted too far into a vertebra. The cannula handle can have a passage so that the cannula and handle form a continuous passage. Additionally, the pedicle access tool can have a stylet comprising a needle handle detachably coupled to the cannula handle and a needle coupled to the needle handle. The needle can pass through the continuous passage and comprising a needle tip that extends past the tip of the cannula.

One embodiment of a fusion method can comprise guiding a dilator to a surgical site on the posterior side of a first vertebra to create a working passage to the surgical site at the first vertebra; guiding a rasp down a rasp guide to the surgical site and roughening bone at the surgical site using the rasp; guiding a piece of bone fusion promoting material down a bone fusion promoting material guide to the site; guiding a first bone anchor down a k-wire to the surgical site; installing the first bone anchor so that a shaft of the first bone anchor passes through the hole in the piece of bone fusion promoting material and a collar of the first bone anchor presses the piece of bone fusion promoting material into the first vertebra; installing a second bone anchor to a second vertebra; and securing a spinal stabilization rod between the first and second bone anchors. The rasp guide, tamp guide and bone fusion promoting material guide can each be a k-wire, cannula or other guide. According to one embodiment, the rasp guide, tamp guide and bone fusion promoting material guide can each be the cannula of a pedicle access tool. Bone fusion promoting material can be positioned to promote posterolateral fusion.

BRIEF DESCRIPTION OF THE DRAWINGS

A more complete understanding of the embodiments and the advantages thereof may be acquired by referring to the following description, taken in conjunction with the accompanying drawings in which like reference numbers indicate like features and wherein:

FIG. 2 is a diagrammatic representation of one embodiment of a cannula;

FIG. 3 is a diagrammatic representation of an embodiment of a cannula tip;

FIG. 4 is a diagrammatic representation of another view of a cannula;

FIG. 5 is a diagrammatic representation of a tool handle;

FIG. 6 is a diagrammatic representation of a stylet;

FIG. 7 is a diagrammatic representation of a portion of an embodiment of a pedicle access tool;

FIG. 8A is a diagrammatic representation of a portion of an embodiment of a pedicle access tool with a trocar tip;

FIG. 8B is a diagrammatic representation of a portion of an embodiment of a pedicle access tool with another embodiment of a tip;

FIG. 13 is a diagrammatic representation of an embodiment of a dilator;

FIG. 14 is a diagrammatic representation of an embodiment of a tap;

FIG. 22 is a diagrammatic representation of another embodiment of using an offset rasp;

FIG. 23 is a diagrammatic representation of another embodiment of using an offset rasp;

FIG. 24 is a diagrammatic representation of an embodiment of implanting bone fusion promoting material;

FIG. 25 is a diagrammatic representation of an embodiment of using a tamp;

FIG. 26 is a diagrammatic representation of an embodiment of installing a k-wire;

FIG. 27 is a diagrammatic representation of an embodiment of removing a cannula;

FIG. 28 is a diagrammatic representation of an embodiment of a k-wire installed in bone;

FIG. 29 is a diagrammatic representation of an embodiment of using a rasp;

FIG. 30 is a diagrammatic representation of an embodiment of using an offset rasp;

DETAILED DESCRIPTION

As used herein, the terms "comprises," "comprising," "includes," "including," "has," "having" or any other variation thereof, are intended to cover a non-exclusive inclusion. For example, a process, product, article, or apparatus that comprises a list of elements is not necessarily limited to only those elements but may include other elements not expressly listed or inherent to such process, process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead these examples or illustrations are to be regarded as being described with respect to one particular embodiment and as illustrative only. Those of ordinary skill in the art will appreciate that any term or terms with which these examples or illustrations are utilized encompass other embodiments as well as implementations and adaptations thereof which may or may not be given therewith or elsewhere in the specification and all such embodiments are intended to be included within the scope of that term or terms. Language designating such non-limiting examples and illustrations includes, but is not limited to: "for example," "for instance," "e.g.," "in one embodiment," and the like. Reference is now made in detail to the exemplary embodiments of the disclosure, examples of which are illustrated in the accompanying drawings. Wherever possible, like numerals will be used throughout the drawings to refer to like and corresponding parts (elements) of the various drawings.

Figure 1:
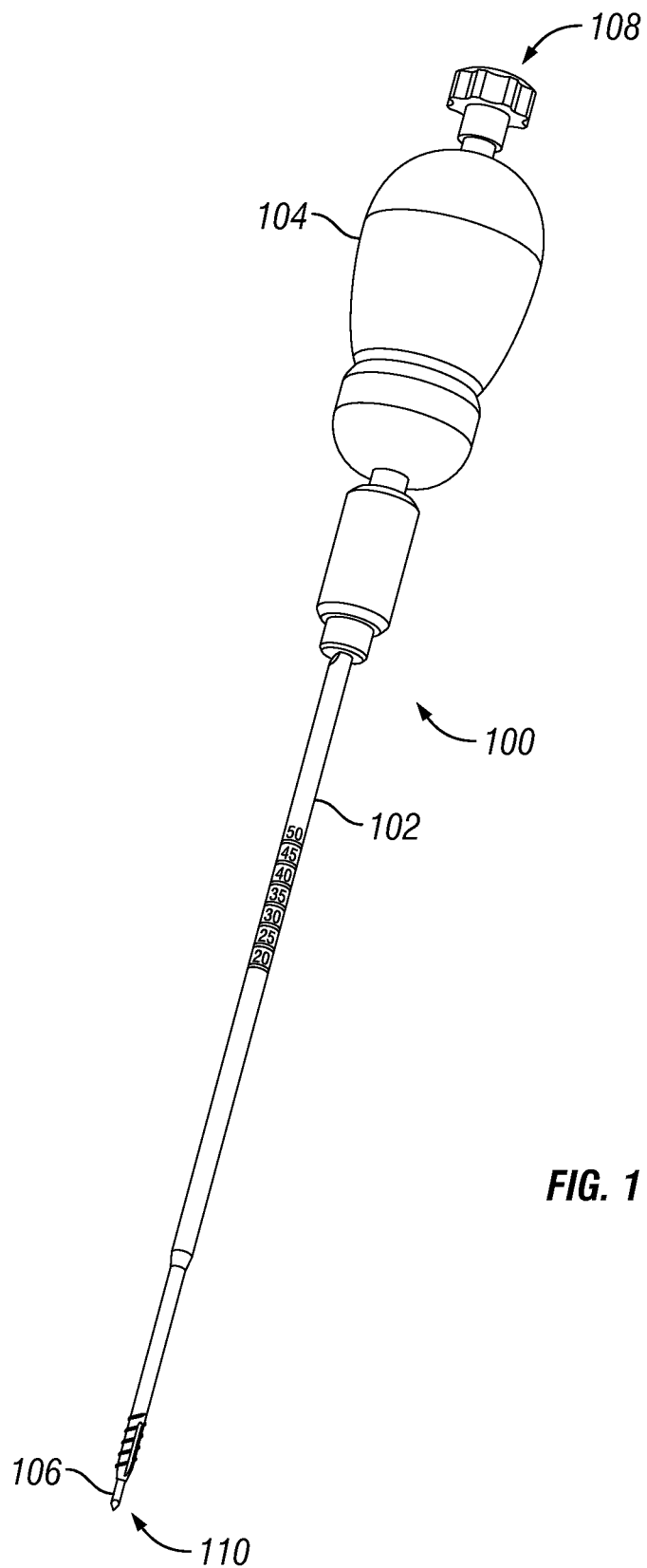
FIG. 1 is a diagrammatic representation of one embodiment of a pedicle access tool.

Embodiments described herein provide a tool that increases the ease of installing bone screws and facilitates methods for posterolateral fusion. FIG. 1 is a diagrammatic representation of a pedicle access tool (PAT) 100 that can be used to prepare a vertebra for a bone screw and to facilitate posterolateral fusion.

In the embodiment of FIG. 1, PAT 100 comprises a cannula 102, a cannula handle 104 detachably coupled to cannula 102 and a stylet 106 that projects from cannula 102 and is removably coupled to handle 104. Cannula 102 and handle 104 form a continuous passage from proximate end 108 to distal end 110. According to one embodiment, the continuous passage is long enough to extend from a surgical site to the exterior of a patient's body.

FIG. 2 is a diagrammatic representation of one embodiment of cannula 102 and FIG. 3 is a diagrammatic representation of an end portion of cannula 102. Cannula 102 can define a passage 111 running from a proximate end 112 to a distal end 114. Cannula can include one or more features, such as indent 116, area 118 or other features to promote quick connection with handle 104. While a particular quick-connect embodiment is shown for an industry standard AO quick connect, embodiments of cannula 102 can include features compatible with any desired quick connect fitting. In other embodiments cannula 102 can include threads or fittings to detachably couple to handle 104.

The tip 120 of cannula 102 can have a shape that is selected so that the tip 120 can perforate cortical bone such that cannula 102 acts as a bone awl. According to one embodiment, tip 120 can be a conical or other shape that transitions from a smaller to a larger diameter.

Cannula 102 can also include a threaded tap section 122 that is selected to tap a hole made by stylet 106 and tip 120. Tip 120 can transition directly into tap section 122 or there may be some distance between tip 120 and tap section 122. According to one embodiment, cannula 102 can be selected to have a thread major diameter that is the same as or less than the major diameter of the bone screw to be installed. By way of example, but not limitation, tap section 122 can have a major diameter of 4.0 mm for a screw with a major thread diameter of 4.5 mm. In other embodiments, tap section 122 can have a major diameter of 4.0 mm-4.5 mm for a screw with a major diameter of 4.5 mm. In yet another embodiment, tap section 122 can have a smaller major diameter. In some cases, if tap section 122 has too small of a major diameter, subsequent taps may be used. Tap section 122 can have any desired length along cannula 102.

In one embodiment, cannula 102 can have a generally cylindrical shape with a first section 124 and a second section 126. First section 124 can have a larger or smaller diameter than second section 126. In one embodiment in which first section 124 has a larger diameter than second section 126, tap section 122, has a major diameter that is less than or equal to the diameter of first section 124. Second section 126 can have a length selected so that pedicle access tool 100 only taps into a vertebra until shoulder 125 contacts the vertebra and limits further insertion.

FIG. 4 is a diagrammatic representation of another view of cannula 102 illustrating that tap section 122 can include a slot 128. Slot 128 can be sized to allow bone material to move into passage 111 when cannula 102 is used to tap bone. Cannula 102 can include other features to aid in surgery including, for example, depth markings 130, size markings or other indicia that can aid in surgery.

FIG. 5 is a diagrammatic representation of tool handle 104. Tool handle 104 can have an ergonomic shape, such as a rounded shape, a "T" shape or other ergonomic shape. Tool handle 104 can include a quick connect 132 to allow for easy detachable connection to cannula 102. While cannula 102 and handle 104 are shown as using an AO quick connect in FIGS. 2 and 5, quick connect 132 can include industry standard quick connect or proprietary quick connect fitting. In other embodiments, tool handle 104 can detachably couple to cannula 102 in other manners such as, but not limited to, using threads, pins or suitable quick connect or non-quick connect connections. Tool handle 104 can connect to cannula 102 so that passage 134 forms a continuous passage with passage 111 of cannula 102. Handle 104 and cannula 102 can, in one embodiment, form a seal so that fluids can flow from cannula 102 through handle 104 without leaking at the connection. Handle 104 can be a ratcheting handle to facilitate tapping.

Handle 104 can also detachably couple to stylet 106. In the example of FIG. 5, handle 104 can include a Luer lock connection, a reverse thread Luer lock connection 136, quick connect connection or other connection to detachably couple to stylet 106. In one embodiment, the connection between handle 104 and stylet 106 can allow stylet 106 to be positioned in various positions so that the tip of stylet 106 extends a desired distance from the tip of cannula 102.

FIG. 6 is a diagrammatic representation of one embodiment of stylet 106 including a stylet handle 138 and stylet needle 140. Needle 140 is long enough so that tip 142 extends beyond tip 120 of cannula 102 (shown in FIG. 7). Tip 142 of needle 140 can be sharp enough to sink into pedicle bone. Handle 138 can include threads 144 or other connection to detachably couple to handle 104. Handle 138 can have a shape that is selected so that it is relatively easy for a surgeon to uncouple stylet 106 from handle 104 and withdraw stylet 106 from PAT 100.

FIG. 7 is a diagrammatic representation of one embodiment of a portion of PAT 100 proximate to distal end 110 including tip 142 of needle 140, tip 120 of cannula 102 and tap section 122 of cannula 102. The tip 142 can extend a select distance beyond tip 120 so that there is a desired distance "d1" to the start of tap section 120. In one embodiment d1 can be 20 mm. In other embodiments, d1 range from 5 mm to 30 mm. Other distances can be used as needed or desired for a particular procedure. As discussed above, the connection between handle 104 and stylet 106 can, in an embodiment, allow the surgeon to select how far tip 142 extends beyond cannula 102 to achieve a desired d1.

Tip 142 can have various configurations. FIG. 8A, for example, is a diagrammatic representation showing a trocar tip while FIG. 8B is a diagrammatic representation showing another embodiment of a tip. It should be understood that tip 142 can have any suitable shape for piercing vertebral bone, including, but not limited to, beveled and trocar tips.

Figures 9A, 9B:
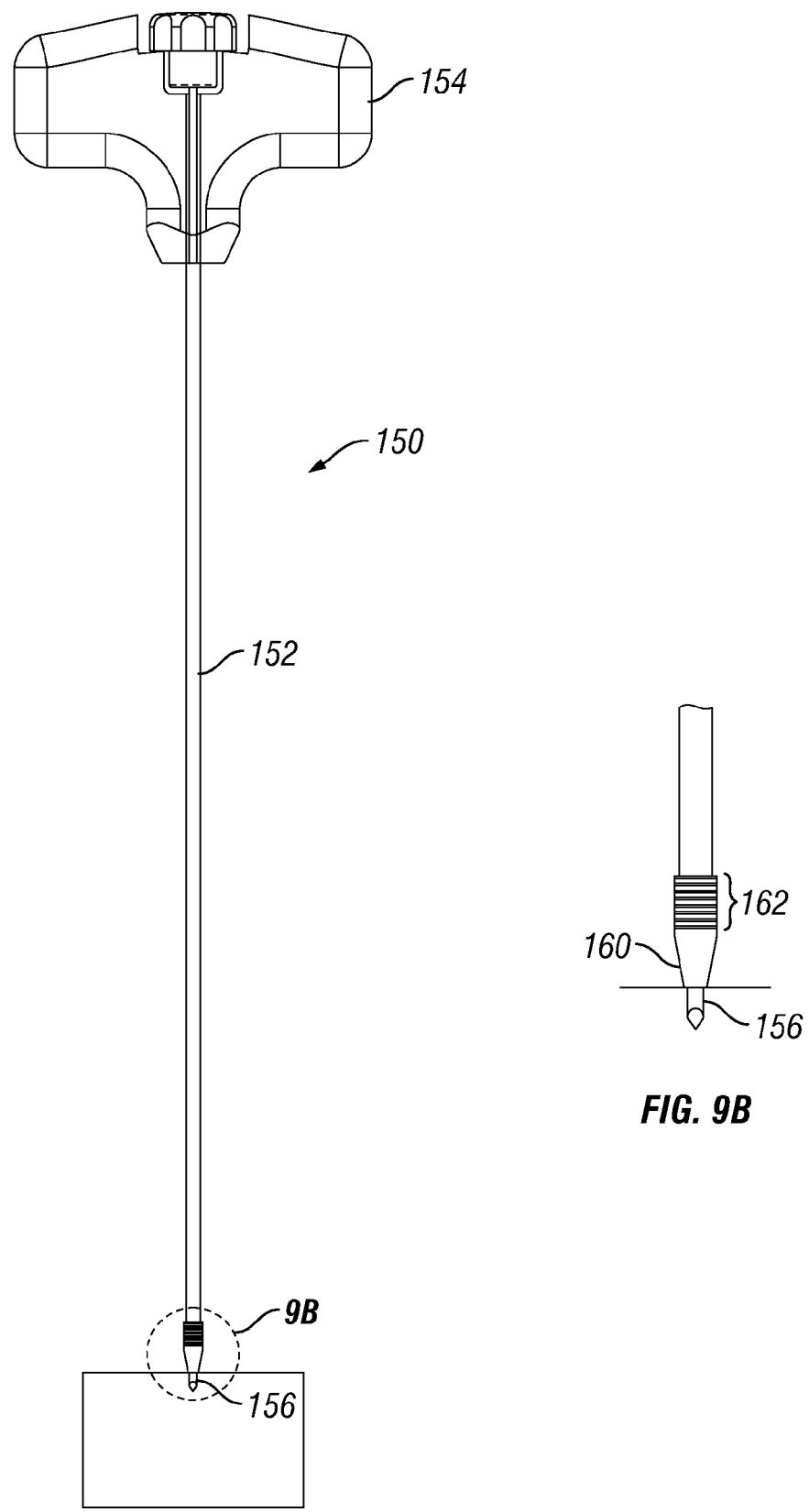
FIGS. 9A and 9B are diagrammatic representations of another embodiment of a pedicle access tool.

FIG. 9A illustrates another embodiment of a PAT 150 having a cannula 152, handle 154 and stylet 156 extending from cannula 152. In the embodiment of FIG. 9A, handle 154 is a "T" shaped handle and cannula 152 has a constant diameter along most of its length. FIG. 9B illustrates a portion of PAT 150 showing tip 160, tap section 162 and stylet tip 166. Stylet tip 156 can be sufficiently sharp to pierce vertebral bone. Tip 160 of cannula 152 can have tapered, conical or other shape that allows cannula 152 to act as an awl to puncture through the cortical bone of the vertebra. Tap section 162 can include a set of mini-threads that allow cannula 152 to be screwed into the hole formed by tip 160. The threads, in one embodiment, can have a smaller diameter and smaller pitch than the threads of the bone screw to be inserted. According to one embodiment, the same cannula 152 can be used regardless of the size screw being inserted and subsequent taps can be used to increase the diameter of the hole.

Embodiments of pedicle access tools can include a cannula and needles formed of biocompatible materials including titanium, PEEK, stainless steel or other material. Although cannula 102 may have some flexibility, it can be rigid enough so that, unlike a k-wire, it does not easily bend when manipulated or bumped by a surgeon. Portions of the tool not inserted into the body can be made of metal, plastic or other suitable material. The pedicle access tool can be formed of a sterilized material and be disposable or constructed to be autoclaved. In one embodiment, cannula 102 and needle 140 can be formed of a material that can be discerned during medical imaging such as fluoroscopy, while the handles are made of a radiolucent material.

Embodiments of a pedicle access tool can act as an awl, tap and cannula reducing the number of tools required for a surgery. Furthermore, because the cannula can thread into the vertebra, the cannula can be secured to the bone during surgery. Consequently, the cannula, rather than a k-wire, can be used to guide some tools to a surgical site. Tools such as rasps, tamps, dilators, taps and others can be adapted to use cannula 102 as a guide.

Figure 10:
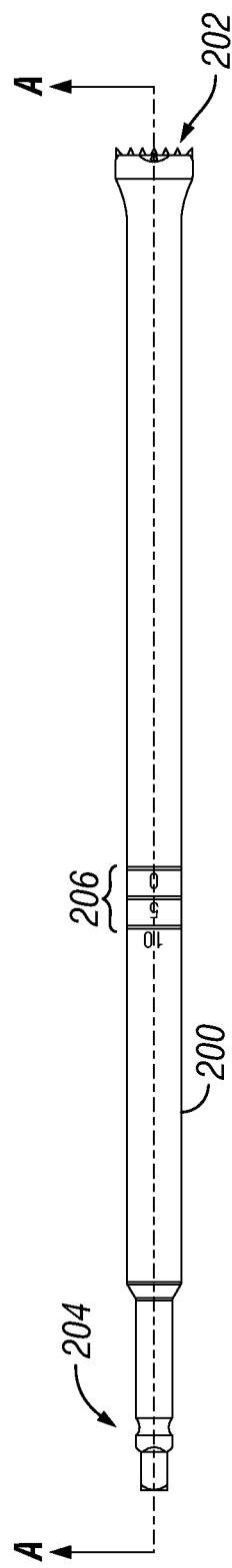
FIG. 10 is a diagrammatic representation of one embodiment of a rasp.

FIG. 10 is a diagrammatic representation of one embodiment of a bone rasp 200 that includes a rasp end 202 having teeth or other features adapted to roughen, bloody or otherwise prepare the surface of a vertebra for bone graft material. Rasp 200 can also include a portion 204 adapted for quick connection or other connection to a handle. Rasp 200 can include depth markings 206 or other features to aid in surgery.

Figure 11:
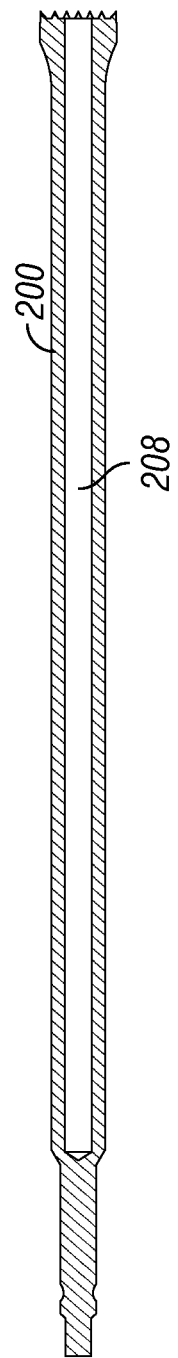
FIG. 11 is a diagrammatic representation of another view of an embodiment of a rasp.

FIG. 11 is a cross-sectional view of one embodiment of bone rasp 200 showing passage 208. Passage 208 is open at rasp end 202 and can have a diameter so that bone rasp 200 can fit over cannula 102. In one embodiment of passage 208 can be as small as possible to preserve the working surface area of rasp end 202 while still allowing rasp 200 to fit over cannula 102. Passage 208 can run through the entire length of rasp 200 or can terminate in rasp 200. Passage 208 can be centered or offset from the center of bone rasp 200. A portion of passage 208 can be open to a slot on the side of rasp 200 so that rasp 200 can be angled relative to cannula 102 as discussed below in conjunction with FIG. 23. The outer of diameter of rasp 200 can be selected so that rasp 200 is small enough to fit inside a selected size dilator.

Figure 12:
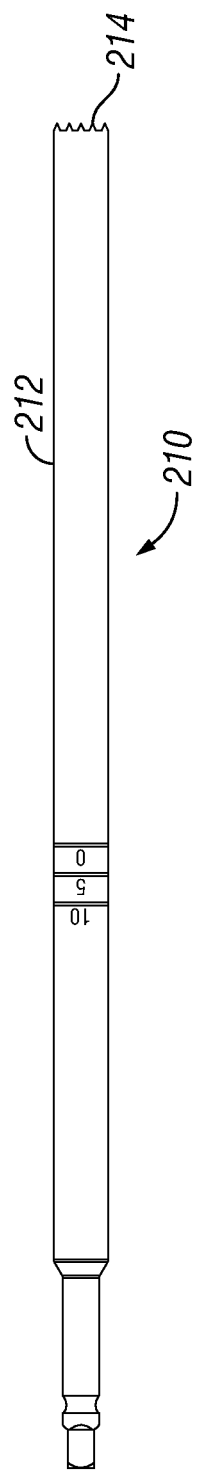
FIG. 12 is a diagrammatic representation of another embodiment of a rasp.

FIG. 12 is a diagrammatic representation of one embodiment of an offset rasp 210 that include a rasp body 212 and a rasp end 214. Rasp end 214 can have teeth or other features adapted to roughen, bloody or otherwise prepare bone for a bone graft. According to one embodiment, rasp 210 can be sized to fit into a dilator next to cannula 102 or a k-wire.

FIG. 13 is a diagrammatic representation of a dilator 220 that defines a passage 222 having a size to accommodate a selected rasp or other tool. Dilator 220 can include an extension 224 having a passage 226 sized to fit over cannula 102 or a k-wire.

FIG. 14 is a diagrammatic representation of a tap 230 that can include a threaded section 232 to tap a hole in preparation for a bone screw. A particular sized tap 230 can be chosen based on the size of bone screw to be inserted. A passage can accommodate cannula 102 or a k-wire so that tap 230 can fit over cannula 102. Tap 230 can include a portion 234 adapted for connection with a handle or can include a non-detachable handle. Tap 230 can include depth markings or other features to aid in surgery.

In operation, PAT 100 can be used to aid in preparing a surgical site for installation of bone screws and to aid in posterolateral fusion. In minimally invasive procedures, a small opening may need to be made in a patient. For example, for a single-level stabilization procedure on one side of the spine, the surgical procedure may be performed through a 2 cm to 4 cm incision formed in the skin of the patient. In some embodiments, the incision may be above and substantially between the vertebrae to be stabilized. In some embodiments, the incision may be above and substantially halfway between the vertebrae to be stabilized. The PAT, dilators, and/or a tissue wedge may be used to provide access to the vertebrae to be stabilized without the need to form an incision with a scalpel through muscle and other tissue between the vertebrae to be stabilized. A minimally invasive procedure may reduce an amount of post-operative pain felt by a patient as compared to invasive spinal stabilization procedures and reduce recovery time for the patient as compared to invasive spinal procedures. Embodiments of posterolateral fusion described herein can be performed as a minimally invasive procedure.

Figure 15C:
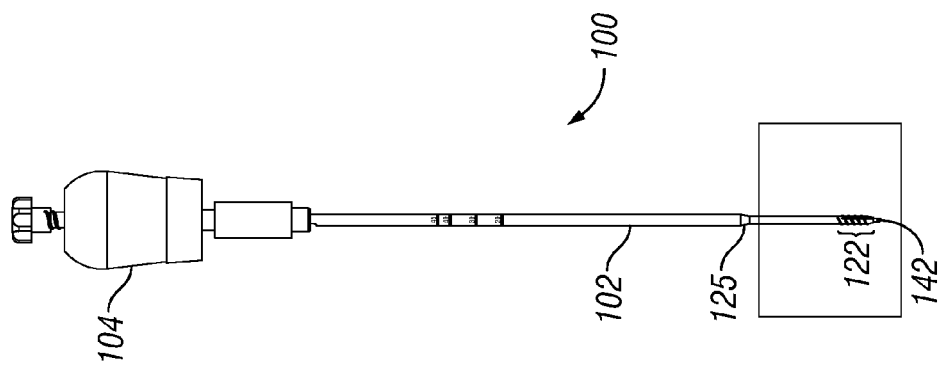
FIGS. 15A-15C are diagrammatic representations of one embodiment of introducing a pedicle access tool to a vertebra.
Figure 15B:
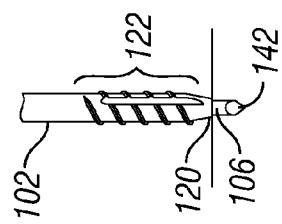
Figure 15A:
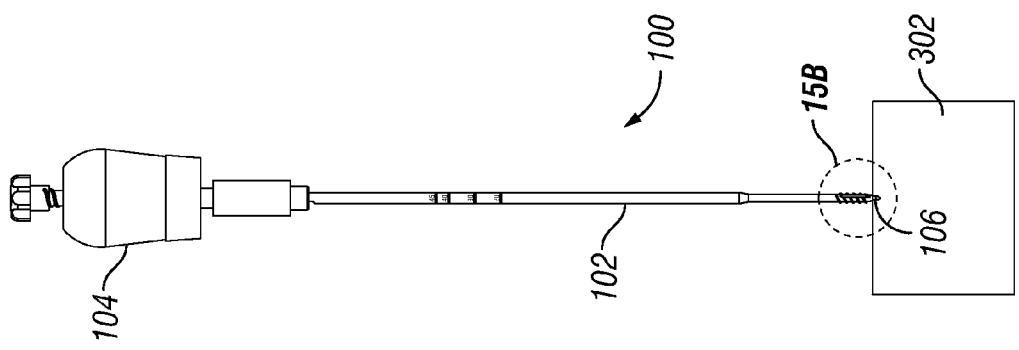

FIGS. 15A, 15B and 15C are diagrammatic representations of introducing PAT 100 into the bone. A surgeon selects the surgical site and guides PAT 100 to the surgical site using medical imaging until tip 142 contacts bone. For posterolateral fusion, the surgical site is the pedicle (represented at 302) of a vertebra. FIG. 15B illustrates tip 142 inserted into the bone. The surgeon can force tip 120 through the bone by gently tapping on handle 104 with a mallet or otherwise driving tip 120 into the cortical bone. PAT 100 can be turned using handle 104 to cause tap section 122 to tap a hole 304 a selected depth as shown in FIG. 15C. Shoulder 125 can prevent PAT 100 from penetrating too deeply into pedicle 302. Thus, it can be seen that PAT 100 can act as a targeting needle, awl and tap in a single tool.

Figure 17:
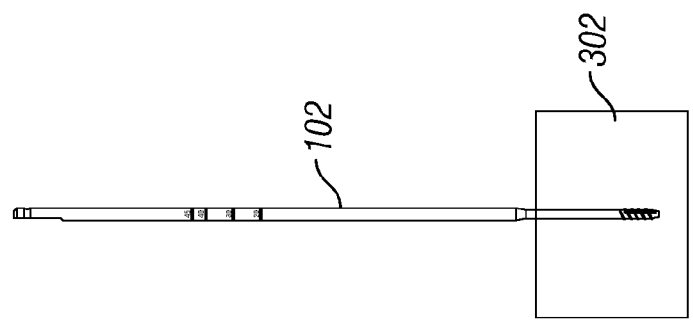
FIG. 17 is a diagrammatic representation of an embodiment of a cannula in a vertebra.
Figure 16:
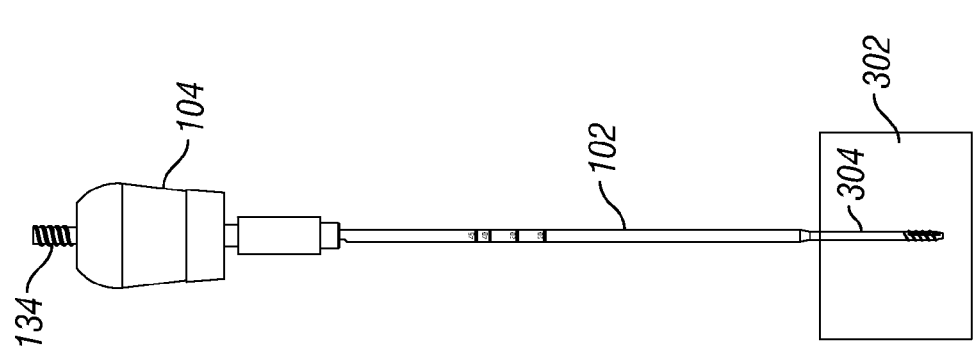
FIG. 16 is a diagrammatic representation of an embodiment of a pedicle access tool with the stylet removed.

In one embodiment, when the hole 304 is a sufficient depth, stylet 106 can be removed. FIG. 16 is a diagrammatic representation of tool 100 in pedicle 302 with stylet 106 removed. According to one embodiment, a syringe can be connected to connection 134 and tissue aspirated through cannula 102 and handle 104. In other embodiments, an aspiration step can occur later or not occur at all. As shown in FIG. 17, handle 104 can be removed.

Figure 18:
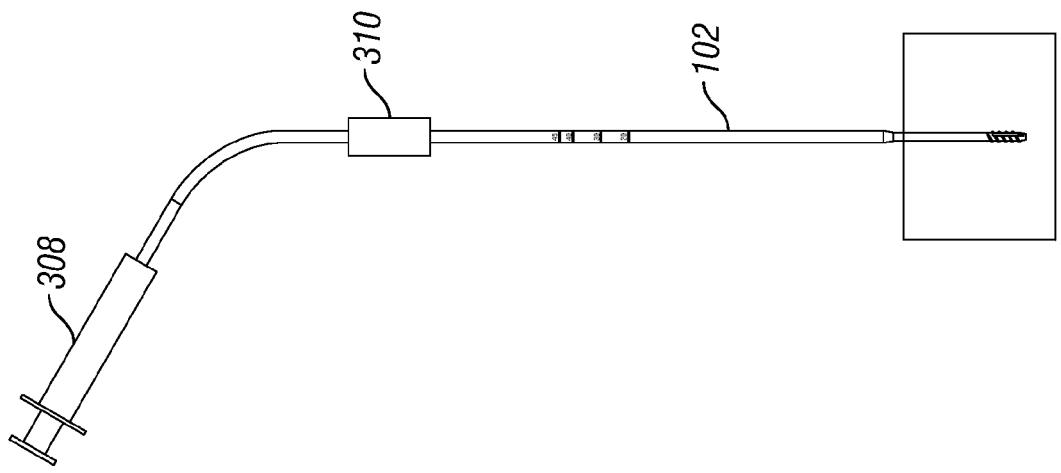
FIG. 18 is a diagrammatic representation of an embodiment of performing aspiration.

As noted above, aspiration can be performed after handle 104 is removed. FIG. 18 is a diagrammatic representation of an embodiment of performing aspiration through cannula 102. A syringe 308 can be connected to cannula 102 using a quick connect adapter 310 or other mechanism to connect to cannula 102. Syringe 308 can be used to aspirate a desired amount of bone marrow or other material through cannula 102.

Figure 19A:
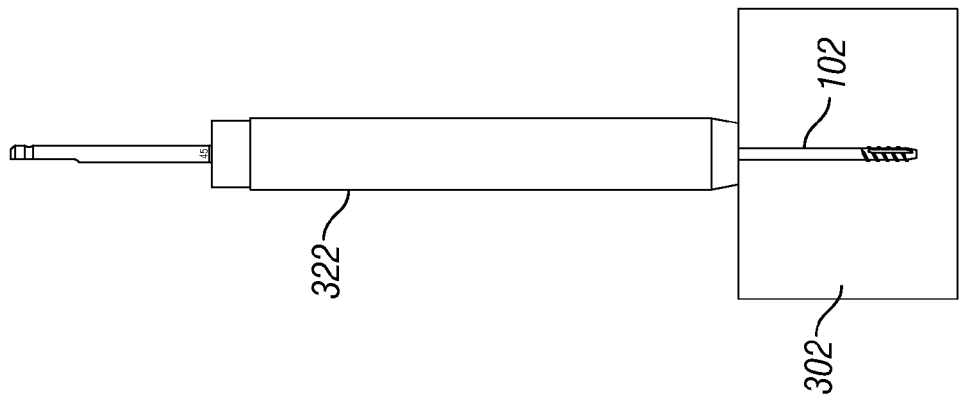
FIGS. 19A-19B are diagrammatic representations of performing dilation.
Figure 19B:
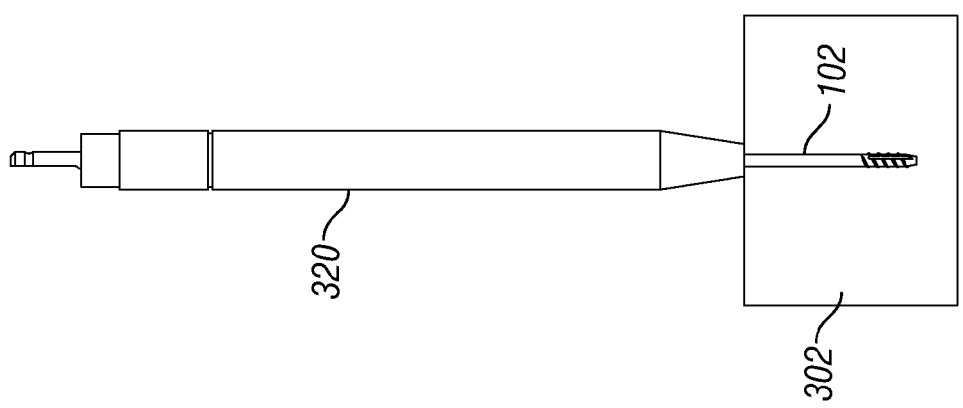

Tissue around cannula 102 can be dilated using one or more dilators that fit over cannula 102 to dilate tissue a desired amount. FIGS. 19A and B, for example, are diagrammatic representations of sequentially dilating tissue about cannula 102 using dilator 320 and then larger dilator 322. According to one embodiment, the depth markings 130 on cannula 102 can show the depth of tip 120 past dilator 322.

Figure 20:
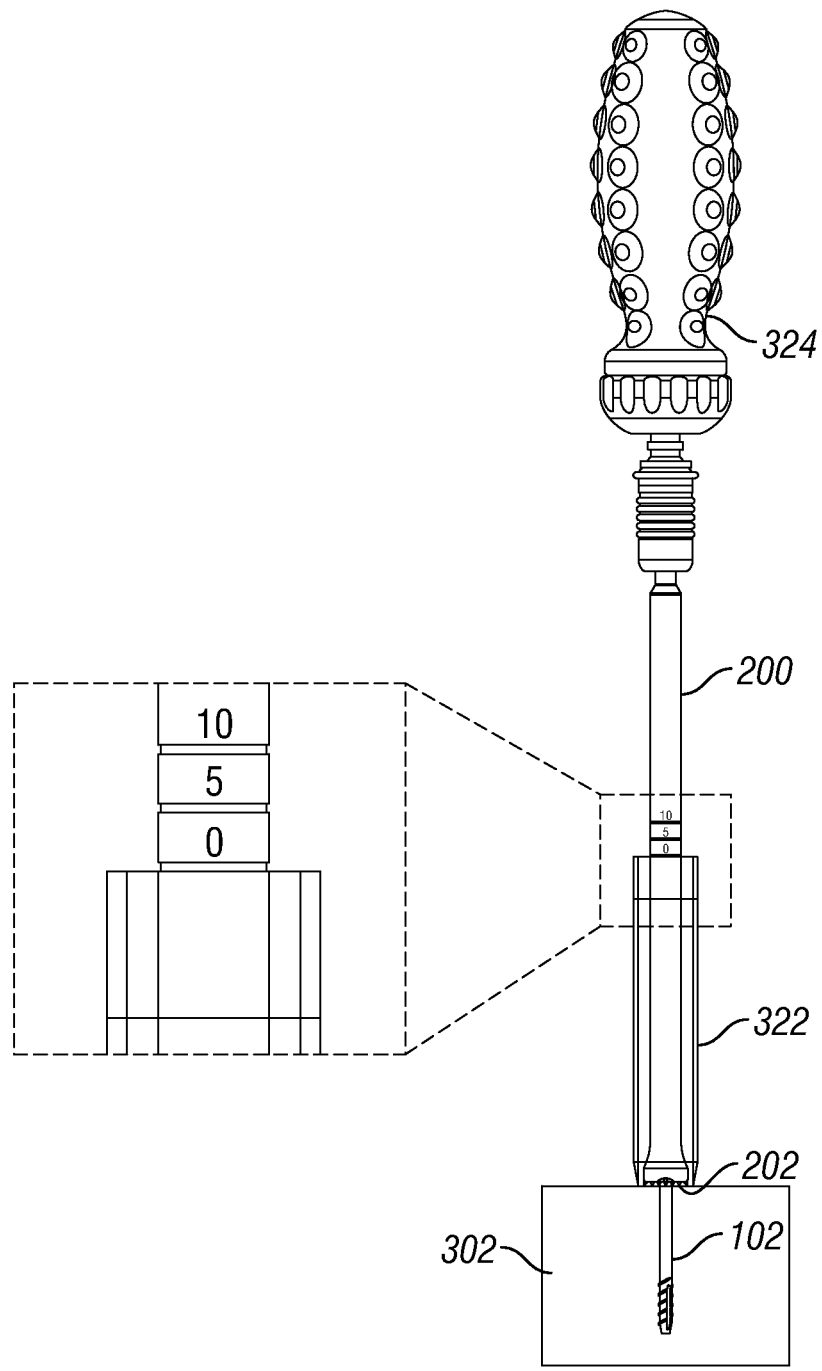
FIG. 20 is a diagrammatic representation of an embodiment of using a rasp.

If a bone graft is to be performed, rasp 200 can be guided down cannula 102 to the vertebra. FIG. 20 is a diagrammatic representation of rasp 200 in place over cannula 102 and inside dilator 322. A handle 324 can be used to manipulate rasp 200. In one embodiment, handle 324 can be the same handle as handle 104 or can be a modular handle used with other tools such as drivers. Depth markings on rasp 200 indicate the depth of rasp end 202 relative to the end of dilator 322. Rasp 200 can be used to de-corticate or otherwise prepare the pedicle surface for a bone graft.

Figure 21:
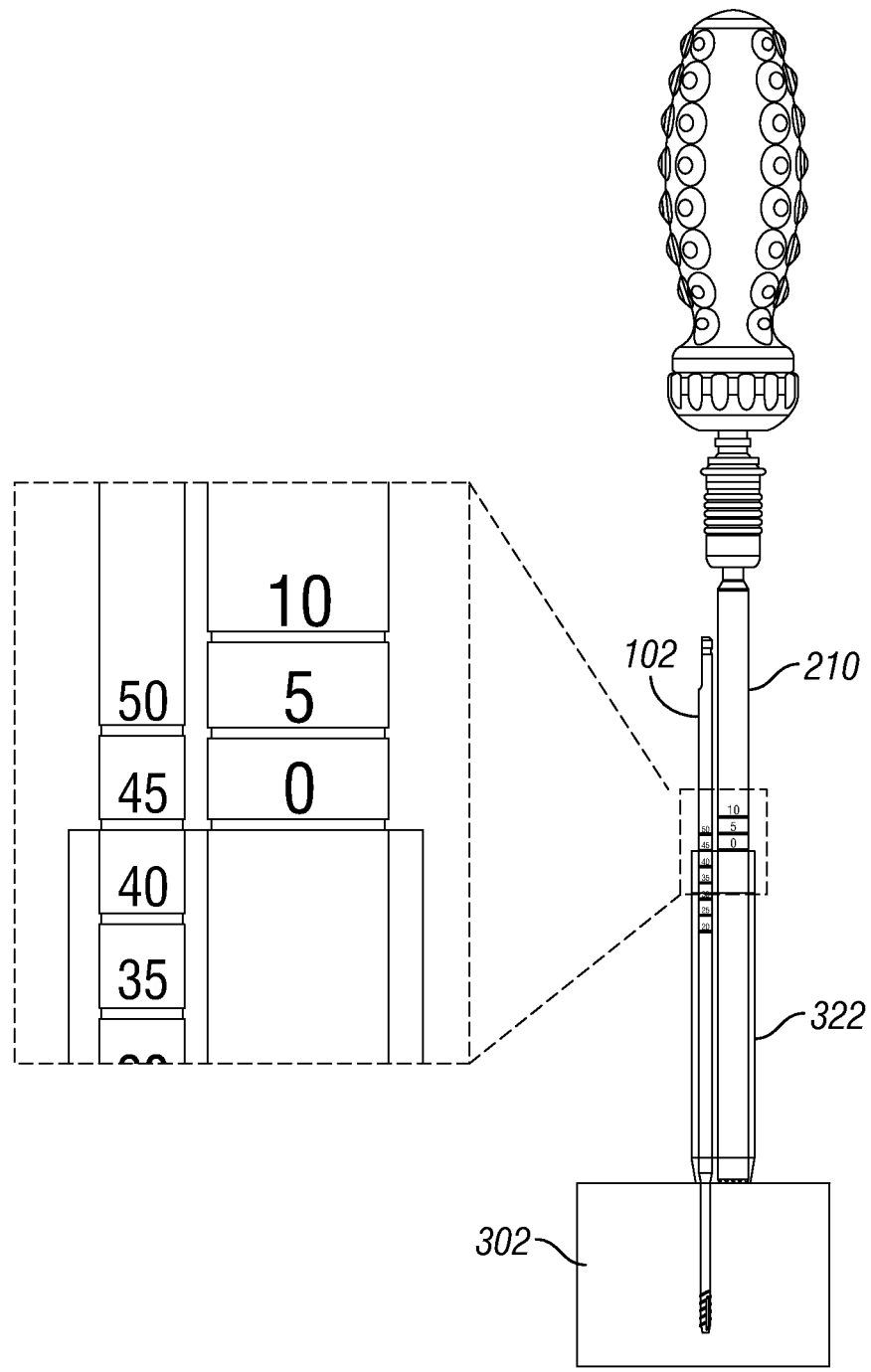
FIG. 21 is a diagrammatic representation of an embodiment of using an offset rasp.

In the example of FIG. 20, rasp 200 is an in-line rasp that is coaxial with cannula 102 and that prepare the bone around cannula 102 up to the diameter of rasp 200. Areas further offset from cannula 102 can be prepared including, for example, inferior and superior facet surfaces. FIG. 21 is a diagrammatic representation of a rasp 210 that fits next to cannula 102 in dilator 322. Rasp 210 and dilator 322 can be moved in a circle around cannula 102 to prepare a larger area. FIG. 22 is a diagrammatic representation of a rasp 210 used in conjunction with a dilator 220. Dilator 220 can be rotated about cannula 102 using extension 224. In one embodiment multiple dilators can be used having different lengths of extension 224 so that rasp 330 can prepare areas closer to and further away from cannula 102.

FIG. 23 is a diagrammatic representation of another embodiment of preparing bone. In the example of FIG. 23 a single rasp 340 can be used to prepare the bone both immediately around and further away from cannula 102. Rasp 340 and dilator 342 can include slots in their walls so that they can tilt relative to cannula 102. Rasp 340 can be oriented coaxial with cannula 102 to prepare an area close to cannula 102 and tilted at various angles to prepare a larger area.

Bone graft or other fusion promoting materials can be placed across de-corticated or otherwise prepared surfaces for posterolateral fusion. Examples of bone fusion promoting materials include, but are not limited to, iliac crest autographs, bone grafts from other sources, bone morphogenetic proteins or other bone fusion materials. FIG. 24 is a diagrammatic representation of one embodiment of introducing bone fusion material. In the embodiment of FIG. 24 a disc of fusion promoting material 350 that has a hole large enough to fit over cannula 102 is lead to the surgical site down cannula 102. The hole can be large enough so that the shaft of a bone screw can pass through the hole, but the collar or head of the bone screw will press disc 350 into the vertebra when the bone screw is secured. In another embodiment, the fusion material can be introduced as particles 352 that can be poured down dilator 320. In some cases, both a disc (or other shaped piece) of bone fusion promoting material and particles can be used together. By way of example, but not limitation, a disc 350 can be used at the center of an area and particles used in a broader area.

A tamp can be used to press the bone graft material into the prepared area. FIG. 25 illustrates and embodiment of a tamp 360 pressing on bone fusion material 350. In the embodiment of FIG. 25, tamp 360 can include a tamp body 362 that is small enough to fit in dilator 322 and a generally flat tamping end 364. Tamp 360 can further include a passage at the center of tamp 360 or offset from the center of tamp 360 that can accommodate cannula 102. While a particular embodiment of an in-line tamp is shown, various embodiments of inline and offset tamps can be similar to previously discussed embodiments of rasps, but with flat or otherwise shaped tamping ends to press the bone fusion material into the prepared bone.

FIG. 26 is a diagrammatic representation of installing a k-wire 400. K-wire 400 can be formed of stainless steel, nitinol or other material. K-wire 400 is advanced through cannula 102 until the tip 404 of k-wire 400 is advanced beyond tip 120 of cannula 102 into the vertebra. A dilator or other support 402 can be used to hold the k-wire straight. If needed, a mallet or other tool can be used to drive the k-wire. Installation of the k-wire can be monitored under Fluoroscopy or other medical imaging.

FIG. 27 is a diagrammatic representation of one embodiment of removing cannula 102. According to one embodiment, handle 104 can be lead down k-wire 400 and reattached to cannula 102. Cannula 102 can then be unthreaded from the vertebral body leaving k-wire 400 inserted in the bone through the end of hole 304 as shown, for example, in FIG. 28. K-wire 400 can be used to guide bone screws or other tools to the surgical site.

A spinal stabilization system can be installed in the body using k-wire 400. The spinal stabilization system can include bone anchor assemblies that secure a rigid or dynamic stabilization rod. The bone anchor assemblies can be lead to the surgical site using k-wire 400 according to methods known or developed in the art. If a disc 350 of bone fusion promoting material is inserted as described above, the shaft of a bone anchor assemblies can pass through the hole in disc 350 while the collar presses bone fusion promoting material into the respective vertebrae. Over time, discs 350 or other bone fusion material will promote bone growth between the vertebrae to cause vertebrae to fuse together adding stability to the spine.

Using cannula 102 as a guide provides the advantage of using a k-wire for fewer steps. Because tip 120 is relatively blunt compared to the tip of a k-wire, it is less likely that cannula 120 will push through a vertebra if inadvertently pushed during surgery. Furthermore, cannula 102 can be easier to manage because it is more rigid than a k-wire and can remain in one place during surgery.

However, various steps described above can be performed using k-wire 400 as a guide rather than cannula 102. Various tools can be sized to fit over the k-wire. These may be the same tools that can fit over cannula 102 or can be tools with smaller diameter passages that can be guided down the k-wire 400. The k-wire 400 can be installed using PAT 100 or other targeting needle. If PAT 100 is not used, separate awls and taps can guided down k-wire 400 to form hole 304.

In particular, k-wire 400 can be used as a guide for any number of steps for promoting posterolateral fusion. FIG. 29 is a diagrammatic representation of rasp 600 in place over k-wire and inside dilator 322. A handle can be used to manipulate rasp 600. In one embodiment, the handle can be the same handle as handle 104 or can be a modular handle used with other tools such as drivers. Rasp 600 can be selected so that the depth markings on rasp 600 indicate the depth of rasp end 602 relative to the end of dilator 322. Rasp 600 can be used to de-corticate or otherwise prepare the pedicle surface for a bone graft. Rasp 600 can be similar to rasp 200, but can have a smaller passage to accommodate k-wire 400. In other embodiments, a rasp with a larger diameter passage, such as rasp 200, can be used over k-wire 400.

Figure 31:
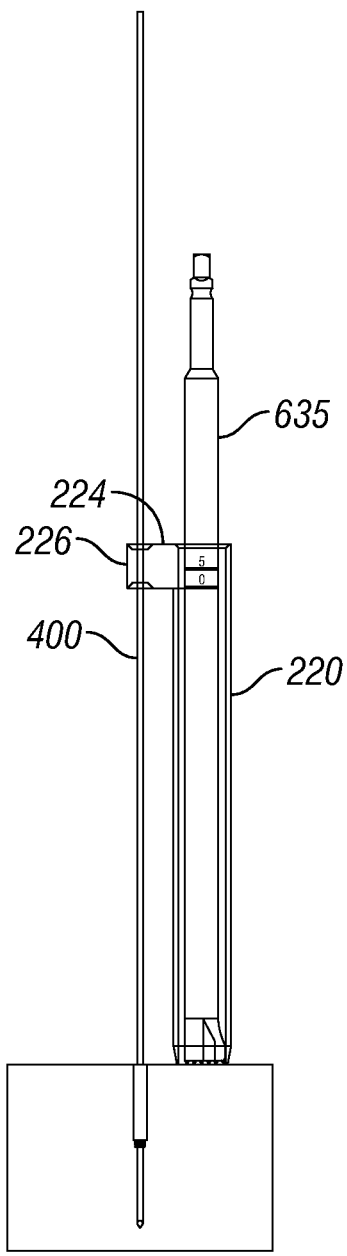
FIG. 31 is a diagrammatic representation of another embodiment of using an offset rasp.

In the example of FIG. 29, rasp 600 is an in-line rasp that is coaxial with k-wire 400 and prepares the bone around cannula k-wire 400 up to the diameter of rasp 600. Areas further offset from k-wire 400 can be prepared including, for example, inferior and superior facet surfaces. FIG. 30 is a diagrammatic representation of using a rasp 635 that fits in dilator 322 next to k-wire 400. Dilator 322 can be rotate about k-wire 400 so that rasp 635 can prepare a larger area. FIG. 31 is a diagrammatic representation of a rasp 638 used in conjunction with a dilator 220. Dilator 220 can be rotated about k-wire 400 using extension 224. In one embodiment multiple dilators can be used having different lengths of extension 224 so that rasp 330 can prepare areas closer to and further away from cannula k-wire 400. While, in this example, extension 224 can be sized to fit over either cannula 102 or k-wire 400, in other embodiments, extension 224 can be sized to fit over k-wire 400 but not cannula 102.

Figure 32:
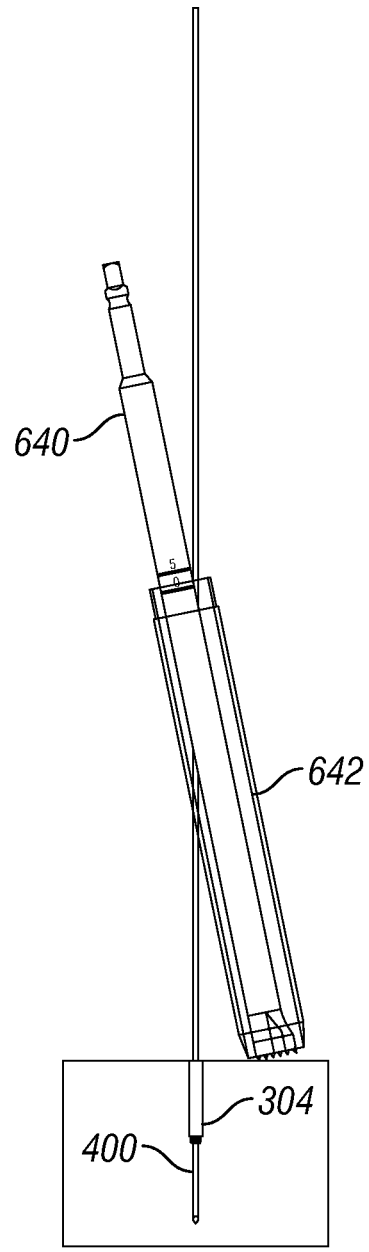
FIG. 32 is a diagrammatic representation of another embodiment of using an offset rasp.

FIG. 32 is a diagrammatic representation of another embodiment of preparing bone. In the example of FIG. 37 a single rasp 640 can be used to prepare the bone both immediately around and further away from k-wire 400. Rasp 640 and dilator 642 can include slots in their walls so that they can tilt relative to cannula k-wire 400. Rasp 640 can be oriented be coaxial with k-wire 400 or tilted at various angles relative to k-wire 400 to prepare a larger area.

Figure 33:
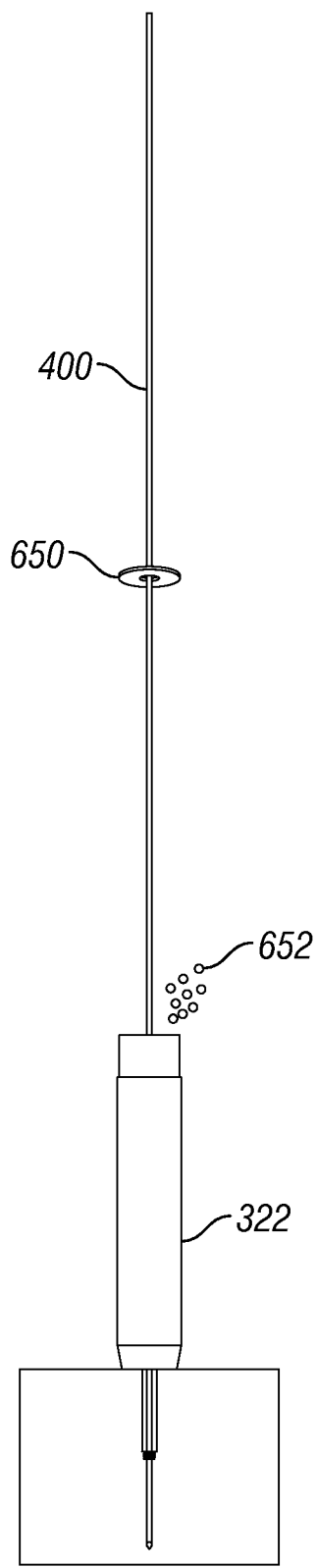
FIG. 33 is a diagrammatic representation of an embodiment of implanting bone fusion promoting material.

FIG. 33 is a diagrammatic representation of one embodiment of introducing bone fusion material. In the embodiment of FIG. 33 a disc of fusion promoting material 650 has a hole that is large enough to fit over k-wire 400 so that it can be lead to the surgical over k-wire 400. According to one embodiment, the hole can be large enough so that the shaft of a bone screw can pass through the hole, but the collar or head of the bone screw will press disc 650 into the vertebra when the bone screw is secured. FIG. 33 also illustrates that bone fusion material can be introduced as particles 652 that can be poured down dilator 322 rather than or in addition to using disc 650.

Figure 34:
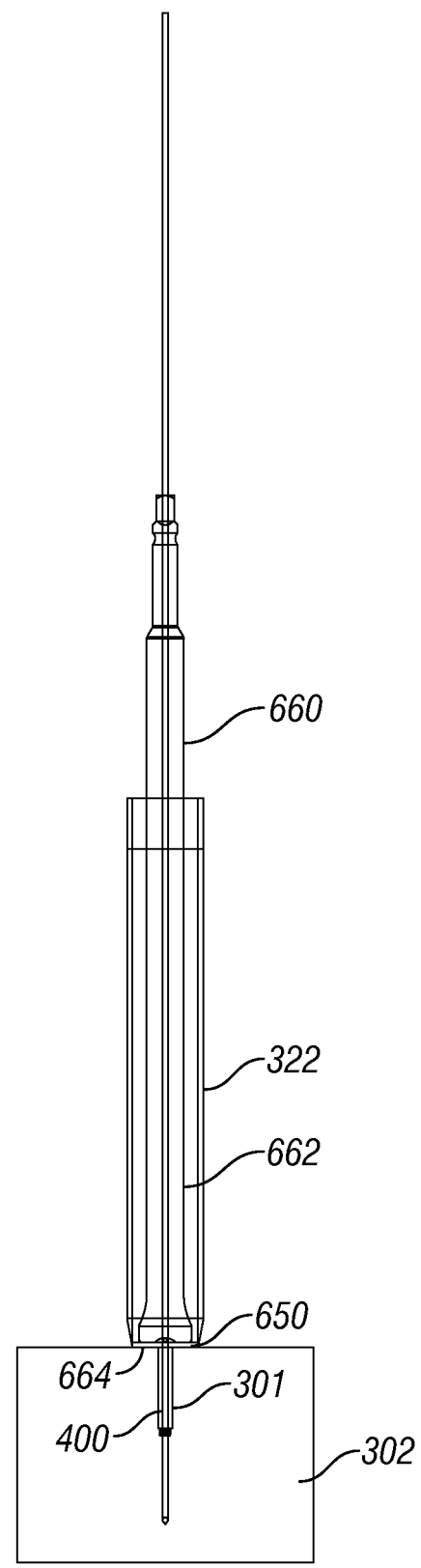
FIG. 34 is a diagrammatic representation of an embodiment of using a tamp.

A tamp can be used to press the bone graft material into the prepared area. FIG. 34 illustrates an embodiment of a tamp 660 pressing on bone fusion material 650. In the embodiment of FIG. 34, tamp 660 can include a tamp body 662 that is small enough to fit in dilator 322 and a generally flat tamping end 664. Tamp 660 can further include a passage at the center of tamp 660 or offset from the center of tamp 660 that can accommodate k-wire 400. While a particular embodiment of an in-line tamp is shown, various embodiments of in-line and offset tamps can be similar to previously discussed embodiments of rasps but with flat or otherwise shaped tamping ends to press the bone fusion material.

Thus, k-wire 400 can also be used as guide in various steps of a posterolateral fusion procedure. The k-wire can be introduced using a targeting needle or PAT 100. In the case in which k-wire 400 is used in conjunction with PAT 100, k-wire 400 can be introduced at any time after the initial hole is formed and any number of the steps can be performed using either cannula 102 or k-wire 400 as the guide. For example, PAT 100 can be used to form and tap a hole and then be removed. K-wire 400 can be used as a guide for the remainder of the procedure. As another example, cannula 102 can be used during the rasping stages and the removed while k-wire 400 can be used when bone fusion material is introduced and during tamping. In another embodiment, cannula 102 can be used to guide bone fusion material to a site and k-wire 400 used to guide a tamp to the site. The foregoing are provided by way of example and the steps can be performed in different orders and using either cannula 102 or k-wire 400 as the guide.

Thus, in operation, a rasp can be lead to a surgical site using a rasp guide, a tamp can be lead to the surgical site using a tamp guide, bone fusion promoting material can be lead to the surgical site using a bone fusion promoting material guide. The guide in each step can be a cannula, k-wire or other guide. In particular, the cannula of pedicle access tool can be used as the guide for various steps. Additional tools, such as a tap or other tool, can be lead to a surgical site using a cannula of a pedicle access tool or a k-wire as needed or desired.

Figure 35:
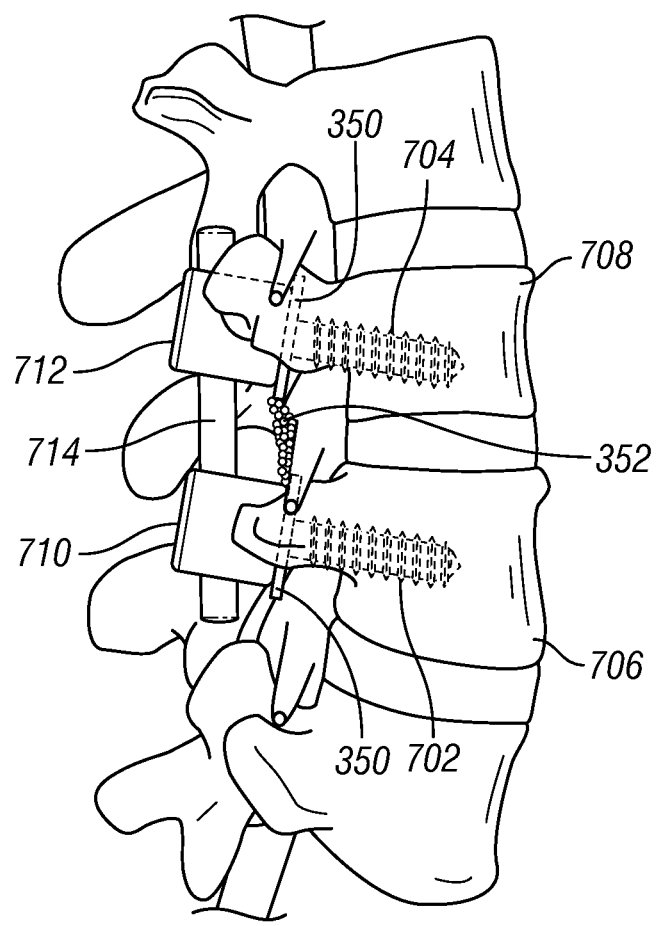
FIG. 35 is a diagrammatic representation of an embodiment of a spinal stabilization system.

FIG. 35 illustrates an embodiment of a spinal stabilization system 700 installed on vertebra prepared to promote posterolateral fusion. Spinal stabilization system 700 can include bone anchors 702 and 704 installed in vertebrae 706 and 708 respectively. Bone anchors 702 and 704 can be polyaxial or monoaxial bone screws or other bone anchors known in the art. The bone anchors can be cannulated so that they can pass over a k-wire. Each bone anchor can include a collar (e.g., collars 710 and 712) that secures a rigid or dynamic spinal stabilization rod 714.

In the embodiment illustrated, collars 710 and 712 press a disc of bone fusion promoting material 350 into an area of the pedicle prepared by a rasp. Additional bone fusion promoting material 352 can be placed further away from bone anchors 702 and 704 to promote a broader region of fusion. Over time, bone will fuse between vertebrae 706 and 708 to stabilize the spine.

While various embodiments of tools have been described with reference to preparing a pedicle, other embodiments can be used to prepare surgical sites at other portions of the vertebrae. Additionally, the steps for a posterolateral fusion described herein can be used to promote fusion at other portions of the spine. Furthermore, while various embodiments have been described as using a k-wire or cannula as a guide for various steps in the fusion procedure, other guides as needed or desired can be used.

In the foregoing specification, the disclosure has been described with reference to specific embodiments. However, as one skilled in the art can appreciate, embodiments of the tools and methods disclosed herein can be modified or otherwise implemented in many ways without departing from the spirit and scope of the disclosure. Accordingly, this description is to be construed as illustrative only and is for the purpose of teaching those skilled in the art the manner of making and using other embodiments. It is to be understood that the forms of the disclosure herein shown and described are to be taken as exemplary embodiments. Equivalent elements or materials may be substituted for those illustrated and described herein. Moreover, certain features of the disclosure may be utilized independently of the use of other features, all as would be apparent to one skilled in the art after having the benefit of this description of the disclosure.

What is claimed is:

1. A method for spinal fusion comprising:
    first, providing a pedicle access tool comprising:
        a cannula defining a passage from a proximate end to a distal end, the cannula further comprising:
            a tip adapted to act as an awl;
            a set of male threads adapted to act as a tap; and
        a needle disposed in the passage having a needle tip extending from the distal end of the cannula;
    second, with the needle disposed in the passage of the cannula, guiding the needle tip of the pedicle access tool into a pedicle of a vertebra;
    third, puncturing a cortical layer of the vertebra with the tip of the cannula;
    fourth, tapping a hole at the surgical site using the cannula while the needle is in place in the cannula; and
    fifth, after the cannula is inserted into the vertebra, guiding one or more tools over the cannula to the vertebra in a minimally invasive surgical procedure.

2. The method of claim 1, wherein after the step of tapping a hole, the method further comprising:
    removing the needle and leaving the cannula secured in the hole of the surgical site.

3. The method of claim 2, wherein after the step of removing the needle, the method further comprising guiding a rasp over the cannula.

4. The method of claim 3, wherein guiding the rasp over the cannula comprises guiding an inline rasp over the cannula and wherein the method further comprises roughening a first area of bone using the inline rasp.

5. The method of claim 4, further comprising guiding an offset rasp next to the cannula in a dilator and roughening a second area of bone further away from the cannula than the first area of bone.

6. The method of claim 2, further comprising using the cannula to guide bone fusion promoting material to the surgical site, wherein the bone fusion promoting material comprises a piece of material defining a hole to fit over the cannula.

7. The method of claim 6, further comprising leading a tamp to the surgical site using the cannula and tamping the bone fusion promoting material.

8. The method of claim 1, further comprising inserting a k-wire through the cannula and then removing the cannula.

9. The method of claim 8, further comprising:
    guiding a first bone anchor to the surgical site using a k-wire; and
    installing the first bone anchor to a first vertebra so that the a shaft of the first bone anchor passes through a hole in a first piece of bone fusion promoting material and a collar of the first bone anchor presses the first piece of bone fusion promoting material into an area of prepared bone at the first vertebra;
    installing a second bone anchor to a second vertebra; and
    securing a spinal stabilization rod between the first and second bone anchors.

10. The method of claim 9, wherein installing the second bone anchor further comprises installing the second bone anchor so that a shaft of the second bone anchor passes through a hole in a second piece of bone fusion promoting material and a collar of the second bone anchor presses the second piece of bone fusion promoting material into the second vertebra.

11. The method of claim 10, further comprising placing additional bone fusion promoting material in an area between the first bone anchor and second bone anchor.

12. The method of claim 1, wherein the cannula has a length, wherein guiding one or more tools over the cannula includes guiding one or more tools over the length of the cannula to the vertebra.

13. A method for posterolateral fusion comprising:
    providing a pedicle access tool comprising:
        a cannula defining a passage from a proximate end to a distal end, the cannula further comprising:
            a tip adapted to act as an awl;
            a set of male threads adapted to act as a tap; and
        a needle disposed in the passage having a needle tip extending from the distal end of the cannula;
    guiding the needle tip of the pedicle access tool into a pedicle of a vertebra;
    puncturing a cortical layer of the vertebra with the tip of the cannula;
    tapping a hole at the surgical site using the cannula while the needle is in place in the cannula;
    removing the needle and leaving the cannula secured in the hole in the vertebra;
    guiding a rasp to the pedicle using the cannula and roughening bone around the cannula using the rasp;
    guiding a first piece of bone fusion promoting material to the pedicle using the cannula, wherein the first piece of bone fusion promoting material defines a hole through which the cannula passes;
    guiding a tamp to the first piece of bone fusion promoting material using the cannula and tamping the first piece of bone fusion promoting material using the tamp;
    installing a k-wire in through the passage defined by the cannula;
    removing the cannula from the pedicle;
    guiding a first bone anchor down the k-wire to the surgical site;
    installing the first bone anchor so that a shaft of the first bone anchor passes through the hole in the piece of bone fusion promoting material and a collar of the first bone anchor presses the piece of bone fusion promoting material into the roughened bone around the cannula;

installing a second bone anchor assembly to a second vertebra; and securing a spinal stabilization rod between the first and second bone anchors.

14. The method of claim 13, wherein installing the second bone anchor assembly to the second vertebra further comprises securing the second bone anchor so that a collar of the second bone anchor presses a second piece of bone fusion promoting material into a roughened area of the second vertebra, wherein the first piece of bone fusion promoting material and second piece of bone fusion promoting material are positioned to promote posterolateral fusion.

15. The method of claim 14, further comprising disposing additional bone fusion promoting material between the first and second pieces of bone fusion promoting material.

\* \* \* \* \*